(12) United States Patent
Ryan et al.

(10) Patent No.: US 10,820,904 B2
(45) Date of Patent: Nov. 3, 2020

(54) SACRIFICIAL COUPLER FOR RELOADABLE HEMOSTASIS CLIPPING DEVICE

(71) Applicant: Boston Scientific Limited, St. Michael (BB)

(72) Inventors: Shawn Ryan, Littleton, MA (US); Joseph W. King, Waltham, MA (US); Boopathi Rajarathnam, New Delhi (IN); Laurie A. Lehtinen, Marlborough, MA (US); Daniel Congdon, Wenham, MA (US); Ramon Estevez, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 257 days.

(21) Appl. No.: 15/714,485

(22) Filed: Sep. 25, 2017

(65) Prior Publication Data

US 2018/0085122 A1 Mar. 29, 2018

Related U.S. Application Data

(60) Provisional application No. 62/401,513, filed on Sep. 29, 2016.

(51) Int. Cl.
*A61B 17/10* (2006.01)
*A61B 17/128* (2006.01)
(Continued)

(52) U.S. Cl.
CPC .......... *A61B 17/10* (2013.01); *A61B 17/1227* (2013.01); *A61B 17/1285* (2013.01);
(Continued)

(58) Field of Classification Search
CPC ....... A61B 17/08; A61B 17/083; A61B 17/10; A61B 17/128; A61B 17/1285
See application file for complete search history.

(56) References Cited

U.S. PATENT DOCUMENTS

| | | | |
|---|---|---|---|
| 5,304,183 A * | 4/1994 | Gourlay | A61B 17/00234 227/901 |
| 6,991,634 B2 * | 1/2006 | Sugiyama | A61B 17/122 606/142 |

(Continued)

FOREIGN PATENT DOCUMENTS

| | | |
|---|---|---|
| DE | 10 2009 022271 | 11/2010 |
| JP | 2007/209775 | 8/2007 |

(Continued)

*Primary Examiner* — Melanie R Tyson
(74) *Attorney, Agent, or Firm* — Fay Kaplun & Marcin, LLP

(57) ABSTRACT

A system for treating tissue includes a clip assembly including a pair of clip arms, proximal ends of the clip arms slidably received within a channel of a capsule to be moved between a tissue receiving configuration and a tissue clipping configuration, an applicator including a catheter and a control member extending therethrough, a distal end of the control member configured to be connected to the clip arms to move the clip assembly between the tissue receiving and tissue clipping configurations, and a coupler releasably coupled to proximal ends of the clip arms and configured to be coupled to the distal end of the control member, the coupler configured to yield when a proximal force exerted on the coupler via the control member exceeds a first predetermined threshold value to disengage the clip arms to deploy the clip assembly.

5 Claims, 2 Drawing Sheets

(51) Int. Cl.
*A61B 17/122* (2006.01)
*A61B 90/00* (2016.01)
*A61B 17/00* (2006.01)
*A61B 17/08* (2006.01)

(52) U.S. Cl.
CPC ..... *A61B 17/083* (2013.01); *A61B 2017/0034* (2013.01); *A61B 2017/00477* (2013.01); *A61B 2017/00818* (2013.01); *A61B 2090/037* (2016.02)

(56) References Cited

U.S. PATENT DOCUMENTS

| | | | |
|---|---|---|---|
| 7,578,072 B2 | 8/2009 | Hayashida | |
| 8,465,501 B2* | 6/2013 | Matsuoka | A61B 17/122 606/142 |
| 2007/0233187 A1 | 10/2007 | Lobello | |
| 2008/0140089 A1* | 6/2008 | Kogiso | A61B 17/1285 606/142 |
| 2014/0379018 A1 | 12/2014 | Martinez | |
| 2015/0018848 A1* | 1/2015 | Kappel | A61B 17/1285 606/140 |

FOREIGN PATENT DOCUMENTS

| | | |
|---|---|---|
| JP | 5038691 | 7/2012 |
| WO | 2009/155286 | 12/2009 |
| WO | 2010/133215 | 11/2010 |
| WO | 2012/151415 | 11/2012 |

\* cited by examiner

SACRIFICIAL COUPLER FOR RELOADABLE HEMOSTASIS CLIPPING DEVICE

PRIORITY CLAIM

The present disclosure claims priority to U.S. Provisional Patent Application Ser. No. 62/401,513 filed Sep. 29, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising a clip assembly, an applicator and a coupler. The clip assembly includes a pair of clip arms, each of the clip arms extending from a proximal end to a distal end, the proximal end of each of the clip arms slidably received within a channel of a capsule to be moved between a tissue receiving configuration, in which distal ends of the clip arms are separated from one another, and a tissue clipping configuration, in which distal ends of the clip arms are moved toward one another. The applicator includes a catheter and a control member extending therethrough, the control member including a distal end configured to be connected to the clip arms to move the clip assembly between the tissue receiving configuration and the tissue clipping configuration. The coupler is releasably coupled to proximal ends of the clip arms and configured to be coupled to the distal end of the control member, the coupler configured to yield when a proximal force exerted on the coupler via the control member exceeds a first predetermined threshold value to disengage the clip arms and deploy the clip assembly.

In an embodiment, the proximal ends of the clip arms may be connected to one another via a connector.

In an embodiment, a distal portion of the coupler may include a plurality of fingers movable between a biased engaging configuration, in which tabs of the plurality of fingers engage the proximal ends of the clip arms, and a non-engaging configuration in which the tabs are moved out of engagement with the clip arms.

In an embodiment, the coupler may include a lumen extending therethrough, the lumen including a first tapered portion tapering from a proximal end toward a narrow opening that deforms when a distal force exerted thereon by an enlarged distal end of the control member exceeds a second predetermined threshold value so that the enlarged distal end may be moved distally therepast to couple the control member to the coupler.

In an embodiment, the lumen of the coupler may include a second tapered portion flaring outward from the narrow opening to a distal end so that when the enlarged distal end of the control member is moved proximally against the second tapered portion, the plurality of fingers is moved from the engaging configuration to the non-engaging configuration.

In an embodiment, the coupler may include an enlarged distal end received within a correspondingly sized and shaped space of the connector.

In an embodiment, the coupler may include an enlarged proximal end sized and shaped to be received within a correspondingly sized and shaped portion of the distal end of the control member.

In an embodiment, the distal end of the control member may be defined via a pair of opposed arms biased toward one another and configured to spread apart when the proximal end of the coupler is pressed thereagainst so that the proximal end of the coupler is moved proximally past a distal opening to be received and held within the correspondingly sized and shaped portion of the distal end of the control member.

In an embodiment, the coupler may be configured to separate at a point proximal of the distal end thereof.

In an embodiment, the coupler may define a distal pair of opposed arms sized and shaped to snap over a correspondingly sized and shaped portion of the clip arms.

In an embodiment, the coupler may define a proximal pair of opposed arms, the proximal pair of opposed arms biased toward one another and configured to spread apart when the distal end of the control member is pressed thereagainst so that the distal end of the control member is moved distally past a proximal opening into a socket sized and shaped to hold the distal end of the control member.

In an embodiment, a force required to disengage the coupler from the clip arms may be smaller than a force required to disengage the coupler from the control member.

The present disclosure also relates to a reloadable clipping device, comprising a clip assembly and a coupler. The clip assembly includes a pair of clip arms, each of the clip arms extending from a proximal end to a distal end, the proximal end of each of the clip arms connected to a connector slidably received within a channel of a capsule to move the clip arms between a tissue receiving configuration, in which distal ends of the clip arms are separated from one another, and a tissue clipping configuration, in which distal ends of the clip arms are moved toward one another. The coupler is releasably coupled to the proximal ends of the clip arms and configured to be coupled to a distal end of the control member so that the clip assembly is movable between the tissue receiving configuration and the tissue gripping configuration via the control member, the coupler configured to yield when a proximal force exerted on the coupler via the control member exceeds a first predetermined threshold value to disengage the clip arms to deploy the clip assembly.

In an embodiment, the coupler may extend from a proximal end to a distal end and includes a lumen extending therethrough, the distal end defining a plurality of fingers movable between a biased engaging configuration, in which tabs of the plurality of fingers engage the proximal ends of the clip arms, and a non-engaging configuration in which the tabs are moved out of engagement with the clip arms, the lumen including first and second tapered portions separated from one another via a narrow opening, the control member coupled to the coupler when an enlarged distal end thereof is moved distally past the narrow opening.

In an embodiment, a distal end of the coupler may be releasably coupled to the connector and a proximal end of the coupler is configured to be coupled to the distal end of the control member.

The present disclosure also relates to a method for treating tissue, comprising loading a clip assembly on an applicator by coupling a control member of the applicator to a coupler that is releasably connected to proximal ends of clip arms of the clip assembly, inserting the loaded clip assembly to a target site within a living body via a working channel of an endoscope, moving the clip assembly between a tissue receiving configuration, in which distal ends of the clip arms are separated from one another, and a tissue clipping configuration, in which distal ends of the clip arms are moved toward one another, by moving the control member longitudinally relative to the locking sleeve until a target tissue is gripped therebetween, as desired, and releasing the clip assembly from the applicator by drawing the control member proximally relative to the clip arms, beyond a predetermined threshold value, so that the coupler yields to disengage the clip arms and at least a portion of the coupler remains connected to the control member.

BRIEF DISCLOSURE

DETAILED DESCRIPTION

Figure 1:
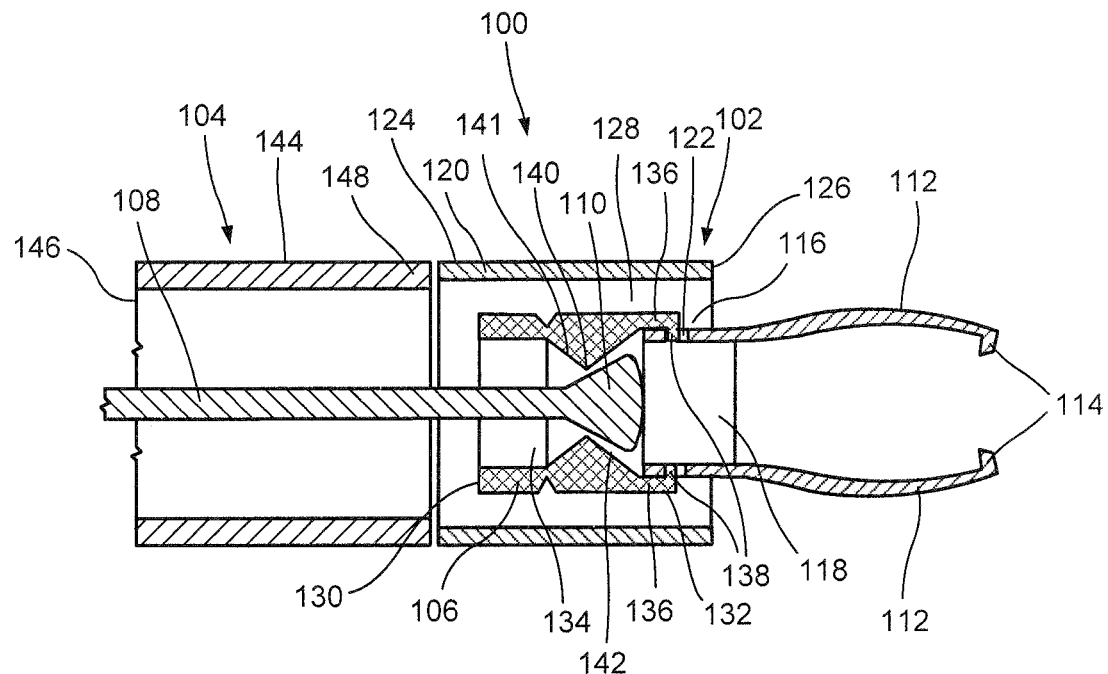
FIG. 1 shows a longitudinal cross-sectional view of a system according to a first exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the applicator assembly includes a coupler for releasably coupling a control member of the applicator to a clip assembly so that multiple clips can be fired using a single applicator assembly. The coupler is pre-assembled with a proximal end of clip arms and is configured to be coupled to a distal end of a control member. When it is desired to deploy the clip assembly in the body, the control member is drawn proximally with respect to the clip assembly until the yields to disengage from the clip arms or fractures to release the clip arms from the control member. It should be noted that the terms "proximal" and "distal," as used herein, are intended to refer to a direction toward (proximal) and away from (distal) a user of the device.

Figure 2:
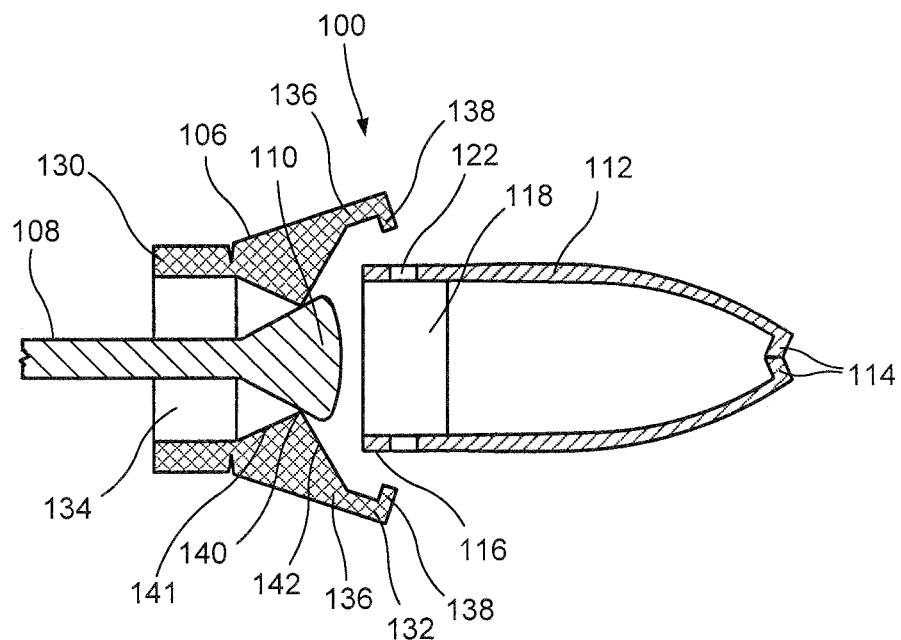
FIG. 2 shows a longitudinal cross-sectional view of the system of FIG. 1, in a deployment configuration.

As shown in FIGS. 1-2, a system 100 according to an exemplary embodiment of the present disclosure comprises a clip assembly 102, an applicator 104 and a coupler 106 facilitating a releasable connection between the applicator 104 and the clip assembly 102. The clip assembly 102 is loadable onto a distal portion of the applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. Each clip assembly 102 according to this embodiment, is pre-assembled with a corresponding coupler 106 that is configured to be coupled to a distal end 110 of a control member 108 of the applicator 104 to releasably couple the clip assembly 102 to the applicator. Once the control member 108 has been connected to the coupler 106, the clip assembly 102 may be moved between an open tissue receiving configuration (in which distal ends 114 of clip arms 112 are separated from one another to receive target tissue therebetween) and a closed tissue gripping configuration (in which the distal ends 114 are drawn toward one another to grip target tissue therebetween) by moving the control member 108 relative to a remaining portion of the applicator as will be described below. Upon clipping of the target tissue, as desired, a proximal force may be exerted in the coupler 106 via the distal end 110 of the control member 108. When the force on the coupler 106 exceeds a predetermined threshold value, the coupler 106 will yield and/or fracture to release the clip assembly 102 from the applicator 104.

The clip assembly 102 includes the pair of clip arms 112, proximal ends 116 of which are, in this embodiment, connected to one another via a connector 118 slidably received within a capsule 120. Each of the clip arms 112 extends from a proximal end 116 to a distal end 114 and the proximal ends 116 of the two clip arms 112 may be connected to one another via the connector 118 which, in this embodiment, is connected to the coupler 106. Thus, when the control member 108 is connected to the coupler 106, the control member 108 may be moved longitudinally with respect to the capsule 120 to move the clip assembly 102 between the tissue receiving and gripping configurations. The clip arms 112 of this embodiment are biased toward the open tissue receiving configuration when not drawn into the capsule 120, the clip arms 112 spread apart from one another to receive tissue therebetween. When the clip arms 112 are drawn into the capsule 120, the capsule 120 constrains the clip arms 112, holding the distal ends 114 thereof together in the tissue clipping configuration.

As would be understood by those skilled in the art, the clip arms 112 may include optional gripping features configured to enhance the gripping of tissue therebetween. For example, the distal ends 114 of the clip arms 112 may include tips extending laterally inward toward one another and/or teeth, protrusions, spikes or other structures configured to grip tissue between the distal ends 114 of the clip arms 112. The clip arms 112 may also include a locking feature configured to lock the clip arms 110 in the tissue gripping configuration, once target tissue has been gripped as desired by the clip arms 112. In one embodiment, one or both of the clip arms 112 includes a locking tab extending laterally outward therefrom configured to engage a portion of the capsule 120 when the clip arms 112 have been drawn into the capsule 120 by a predetermined distance. For example, the locking tabs may be received within correspondingly sized, shaped and positioned locking windows extending laterally through a wall of the capsule 120 to lock the clip arms 112 relative to the capsule 120, in the tissue gripping configuration.

In one exemplary embodiment, the proximal ends 116 of the clip arms 112 may be connected to one another via the connector 118 slidably received within the capsule 120 and configured to be connected to the coupler 106. In one example, the connector 118 is a separate element coupling the clip arms 112 to one another. In another example, the connector 118 is integrally formed with the clip arms 112. The connector 118 may include an engaging feature 122 for engaging the coupler 106. The engaging feature 122 may be configured as, for example, a groove extending about the connector 118, the groove being sized and shaped to receive a corresponding engaging portion of the coupler 106, as will be described in further detail below. In one particular embodiment, the groove extends circumferentially about the connector 118.

The capsule 120 extends from a proximal end 124 to a distal end 126 and includes a channel 128 extending longitudinally therethrough. The channel 128 is sized and shaped to receive the connector 118 and at least proximal portions of the clip arms 112 therein. The proximal end 124 of the capsule 120 may be releasably connected to the applicator 104 in any of a variety of ways. In one embodiment, the capsule 120 engages the applicator 104 in a way that permits the clip arms 112 to be moved relative to the capsule 120 from an initial insertion configuration substantially similar to the tissue gripping configuration, in which the clip arms 112 are constrained via the interior surface of the capsule 120 so that distal ends 114 thereof are proximate and/or in contact with one another, distally toward the tissue receiving configuration. The clip arms 112 are drawn proximally relative to the capsule 120 when target tissue is received therebetween as desired to draw the clip arms 112 toward one another. The capsule 120 will also be moved proximally until the capsule 120 comes into contact with a distal end of the applicator 104. Once the capsule 120 abuts the distal end of the applicator 104, the clip arms 112 may be drawn further proximally relative to the capsule 120, toward the tissue gripping configuration. This releasable connection may be achieved via, for example, a friction fit or a loose snap connection as would be understood by those skilled in the art.

In another embodiment, the capsule 120 may be releasably connected to the applicator 104 in a way such that the capsule 120 is released from the applicator 104 upon disengagement of the coupler 106 from the clip arms 112. For example, a portion of the coupler 106 and/or control member 108 may interface with a coupling mechanism between the capsule 120 and the applicator 104 so that, removal of the coupler 106 therefrom disengages the capsule 120 from the applicator 104.

The coupler 106 extends longitudinally from a proximal end 130 to a distal end 132 and includes a lumen 134 extending therethrough. The lumen 134 is sized and shaped to receive and hold an enlarged distal end 110 of the control member 108 therein. In particular, the lumen 134 includes a first tapered portion 141 and a second tapered portion 142 separated from one another via a narrow opening 140. The first tapered portion 141 tapers distally from a proximal end 170 thereof toward the narrow opening 140 while the second tapered portion 142 tapers proximally from a distal end 172 thereof toward the narrow opening 140. In other words, the lumen 134 tapers from the proximal end 170 thereof toward the narrow opening 140 and flares outward from the narrow opening 140 toward the distal end 172. A cross-sectional area of the lumen 134 at the narrow opening 140 is smaller than a remaining portion of the lumen 134. The cross-sectional area of the narrow opening is also smaller than the enlarged distal end 110 of the control member 108 so that, when the enlarged end 110 is pushed distally therepast, the enlarged end 110 is held in the second tapered portion 142. The coupler 106 of this embodiment is formed of an elastically deformable material biased toward a rest position in which the narrow opening 140 has a diameter smaller than a diameter of the enlarged end 110. As the enlarged end 110 is inserted distally, the enlarged end slides distally against the first tapered portion 141, forcing the narrow opening 140 to deflect radially outward to allow the enlarged end 110 to be moved distally therepast when a distally directed force exerted thereon exceeds a predetermined threshold value. Once the enlarged end 110 moves distally past the narrow opening 140, the coupler 106 deflects back to its resting position wherein a cross-sectional area of the narrow opening 140 is again smaller than the diameter of the enlarged end 110, locking the enlarged end 110 within the coupler 106.

Since the coupler 106 is pre-assembled with the clip arms 112, after the enlarged end 110 moves distally past the narrow opening 140, the control member 108 is connected to the clip arms 112 so that the clip arms 112 may be moved between the tissue receiving configuration and the tissue gripping configuration by advancing the control member 108 distally and withdrawing the control member 108 proximally relative to the capsule 120. In particular, the enlarged distal end 110 is housed within the narrow opening 140 proximally of the connector 118 so that the control member 108 is substantially fixed with respect to the clip arms 112.

A distal portion of the coupler 106 according to this embodiment defines a plurality of fingers 136 movable between an engaging configuration, in which the fingers 136 engage the connector 118 of the clip assembly 102, and a non-engaging configuration, in which the fingers 136 are moved out of engagement with the connector 118. The distal ends 132 of the fingers 136 include tabs 138 extending radially inward to engage the engaging feature 122 of the connector 118, in the engaging configuration. In particular, in the engaging configuration the tabs 138 are received within a groove extending about the connector 118. The fingers 136 are biased toward the engaging configuration so that the coupler 106 remains engaged with the clip arms 112 as the clip assembly 102 is moved between the tissue receiving and the tissue gripping configurations.

Once the clip assembly 102 has been used to grip the target tissue and it is desired to deploy the clip assembly 102, however, the control member 108 may the drawn proximally with respect to the capsule 120 until the clip arms 112 are locked with respect to the capsule 120. As described above, the locking of the clip assembly 102 may occur when the clip arms 112 are drawn proximally to a predetermined position within the capsule 120 so that corresponding locking features of the capsule 120 and the clip arms 112 engage one another. Once the clip assembly 102 is locked in the tissue gripping configuration, the enlarged distal end 110 interfaces with the second tapered portion 142 as the control member 108 is moved proximally relative to the clip assembly 102. In other words, upon locking of the clip assembly 102, further proximal motion of the control member 108 causes enlarged the distal end 110 to slide proximally against the narrow opening 140 of the lumen 134, spreading the distal portion of the capsule 106 open more widely disengaging the fingers 136 from the groove in the connector 118 (i.e., moving from the engaging configuration to the non-engaging configuration). In the non-engaging configuration, the fingers 136 are moved radially away from a central axis of the coupler 106 so that the tabs 138 are moved out of the groove of the engaging feature 122 of the connector 118, as shown in FIG. 2, thereby releasing the clip arms 112 therefrom.

Prior to being loaded on the applicator 104, the clip assembly 102 may be stored in a cartridge configured to facilitate loading of the clip assembly 102 on the applicator 104. The cartridge may be configured as a storage container defining a space therewithin that is sized and shaped to house the clip assembly 102 with the coupler 106. The clip assembly 102 may be housed within the cartridge in the tissue receiving configuration. The cartridge includes a proximal opening through which the distal portion of the applicator 104 may be inserted to be coupled to the clip assembly 102, as will be described in further detail below. The cartridge holds the clip assembly 102 in position to facilitate loading onto the applicator 104.

The applicator 104 includes a catheter 144, a flexible member (not shown) extending proximally therefrom, and the control member 108. A proximal end of the flexible member may be connected to a handle portion. The catheter 144 extends longitudinally from a proximal end 146 connected to the flexible member to a distal end 148 configured to be releasably connected to the capsule 120 of the clip assembly 102. The control member 108 extends through the catheter 144 and the flexible member from the distal end 110 to a proximal end connected to an actuator of the handle portion. The flexible member may be formed as a coil or wire having sufficient flexibility to be passed through even tortuous paths of the living body and, in this embodiment, is sized and shaped to be passed through a working channel of an endoscope or other insertion device. The flexible member, however, may be formed of any other suitable flexible structure so long as the flexible member is capable of providing a force in compression sufficient to counter the tension to be placed on the control member 108 from the clip assembly 102.

An exemplary method for loading the clip assembly 102 to the applicator 104 comprises pushing the enlarged distal end 110 of the control member 108 distally against the narrow opening 140 of the coupler 106, which is pre-assembled with the clip assembly 102, until a distal force applied to the narrow opening 140 exceeds a predetermined threshold value, causing opposite sides of the narrow opening 140 to deflect away from one another permitting the enlarged distal end 110 move distally therepast. After the enlarged distal end 110 passes the narrow opening 140, the narrow opening 140 reverts under its natural bias to a position in which the opening of the narrow opening 140 is smaller than the enlarged end 110 which is then locked within the coupler 106 distally of the narrow opening 140 and proximally of the connector 118 fixing the control member 108 to the clip arms 112. As the control member 108 is being coupled to the coupler 106, the catheter 144 may also be pressed against the capsule 120 to releasably couple the catheter 144 thereto.

As described above, where the clip assembly 102 is housed within a cartridge, the catheter 144 and the distal end 110 of the control member 108 may be inserted through a proximal opening of the cartridge to be coupled to the clip assembly 102, in substantially the same manner as described above. Once the catheter 144 has been releasably connected to the capsule 120 and the enlarged distal end 110 is coupled to the clip arms 112 via the coupler 106, the control member 108 may be moved proximally to draw the clip assembly 102 toward a closed clipping configuration. The entire applicator 104 may then be moved proximally relative to the cartridge to draw the clip assembly 102 out of the cartridge, in the closed configuration, via the proximal opening.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the tissue gripping configuration (e.g., with the catheter 106 constraining the distal tabs 116 toward the non-engaging configuration) to reduce damage and facilitate its passage through the working channel. Upon reaching the site of the target tissue, the clip assembly 102 is advanced out of the distal end of the working channel by moving the control member 108 distally relative to the catheter 144 extending the clip arms 110 distally out of the capsule 120 and moving the clip arms 112 to the tissue receiving configuration. Once the target tissue has been received between the clip arms 112, the clip assembly 102 may be moved toward the tissue gripping configuration so that the target tissue is gripped between the distal ends 114 thereof. The clip arms 112 are moved toward the tissue gripping configuration by drawing the control member 108 proximally with respect to the catheter 144 and the capsule 120. Once the clip assembly 102 is in the tissue gripping configuration, the control member 108 may be drawn further proximally to lock the clip arms 112 with respect to the capsule 120.

To deploy the clip assembly 102, the control member 108 is drawn even further proximally. Since the clip arms 112 are fixed with respect to the capsule 120, the proximal motion of the control member 108 causes the distal end 110 of the control member 108 to slide proximally against the second tapered portion 142 of the lumen 134 such that the fingers 136 of the coupler 106 are moved radially away from a central axis thereof, to the non-engaging configuration. In particular, in the non-engaging configuration, tabs 138 at the distal ends 132 of the coupler 106 are disengaged from the groove of the engaging feature 122 of the connector 118. Thus, the control member 108 is disengaged from the clip arms 112. As described above, the disengagement of the control member 108 from the clip arms 112 also releases the capsule 120 from the catheter 144. Thus, the applicator 104 may be withdrawn proximally from the body, leaving the clip assembly 102 clipped over the target tissue. Upon removal of the applicator 104 from the body, the coupler 106, which remains attached to the distal end 110 of the control member 108, may be removed therefrom by pulling the coupler 106 off of the distal end 110. When a force on the coupler 106 exceeds a predetermined threshold force, the narrow opening 140 yields or deforms to allow the enlarged distal end 110 to be moved therepast so that the coupler 106 may be removed therefrom. If so desired, a new clip assembly 102 is then loaded onto the applicator 104, in the same manner as described above, so that the device may then be used to clip a second portion of tissue. This process may be repeated using the same applicator 104 as many times as needed or desired.

Figure 3:
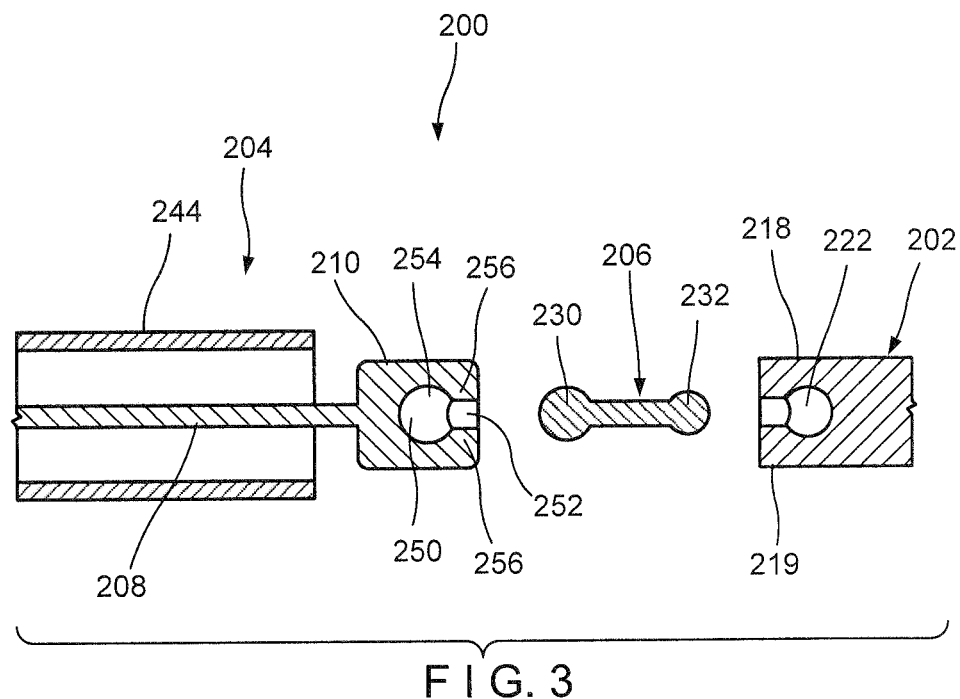
FIG. 3 shows a longitudinal cross-sectional view of a system according to a second exemplary embodiment of the present disclosure.

As shown in FIG. 3, a system 200 according to an exemplary embodiment substantially similar to the system 100 comprises a clip assembly 202 loadable on a distal portion of an applicator 104. In particular, as described above in regard to the system 100, clip arms of the clip assembly 202 may be connected to a control member 208 of the applicator 204 via a coupler 206. The coupler 206 may be pre-assembled with a connector 218, which connects proximal ends of the clip arms together, and is configured to engage a distal end 210 of the control member 208.

The coupler 206, however, extends longitudinally from a proximal end 230 to a distal end 232. The distal end 232 is pre-assembled with the connector 218 at the proximal end of the clip arms. In one embodiment the distal end 232 may be enlarged and substantially ball-shaped. The proximal end 230 may be configured to be coupled to the distal end 210 of the control member 208. In one embodiment, the proximal end 230 may also be enlarged and substantially ball-shaped. The proximal and distal ends 230, 232 of the coupler 206, however, may have any of a variety of shapes and sizes so long as the proximal and distal ends 230, 232 are configured to be coupled to the control member 208 and the connector 218, respectively.

Although the clip arms and capsule are not shown, the clip assembly 202 is substantially similar to the clip assembly 102 described above, including clip arms connected to one another at proximal ends via the connector 218, which is slidably received within the capsule to move the clip arms between a tissue receiving configuration and a tissue gripping configuration. Rather than a groove extending about the connector 218, however, the connector 218 includes a space 222 extending distally from an opening at a proximal end 219 thereof. The space 222 is sized and shaped to receive the distal end 232 of the coupler 206. In one embodiment, the space 222 may be a socket for receiving a ball-shaped distal end 232 of the coupler 206. It will be understood by those of skill in the art, however, that the distal end 232 of the coupler 206 may be assembled with the connector 218 in any of a variety of ways so long as at least a portion of the coupler 206 may be separated therefrom when a force exceeding a predetermined threshold force is exerted thereon. The coupler 206 is coupled to the connector 218 in a manner that allows the clip arms to be moved via movement of the control member 208, when the control member 208 is also coupled to the coupler 206.

The applicator 204 is substantially similar to the applicator 104, described above, comprising a catheter 244 and the control member 208 extending therethrough. The distal end 210 of the control member 208 is similarly configured to be coupled to the coupler 206. Rather than being received within a portion of the coupler, however, the enlarged distal end 210 includes a longitudinal slot 250 extending proximally from a distal opening 252. A proximal portion 254 of the longitudinal slot 250 is sized and shaped for receiving the proximal end 230 of the coupler 206. In one embodiment, the slot 250 may be configured as a socket for receiving a ball-shaped proximal end 230 of the coupler 206. A cross-sectional area of the proximal portion 254 may be larger than a cross-sectional area of the distal opening 252 so that, once the proximal end 230 of the coupler 206 is received within the proximal portion 254, the proximal end 230 is held therein. The longitudinal slot 250 may be defined via opposed portions 256 designed to spread apart when the proximal end 230 is pressed proximally against the distal opening 252. The opposed portions 256 are biased toward one another so that, once the proximal end 230 of the coupler 206 is moved proximally past the distal opening 252 and the proximal end 230 is received within the proximal portion 254, the opposed portions 256 may spring back toward one another to lock the proximal end 230 within the proximal portion 254. Thus, once the proximal portion 230 is received within the proximal portion 254, longitudinal movement of the control member 208 may be used to control a movement of the clip assembly 202 between the tissue receiving and the tissue gripping configurations.

When it is desired to deploy the clip assembly 202 in the living body clipped over a target tissue, the applicator 204 may be disengaged from the clip assembly 204 by drawing the control member 208 proximally relative to the connector 218. When a proximal force on the connector 218 exceeds a predetermined threshold value, the distal end 232 of the coupler 206 may separate from the connector 218. In another embodiment, the coupler 206 may be designed to break or fracture at a point proximal of the distal end 232 so that a remaining portion of the coupler 206 remains coupled to the control member 208. Once the applicator 204 is withdrawn from the body, the portion of the coupler 206 which remains coupled to the control member 208 may be removed therefrom by simply pulling the coupler 206 away from the control member 208. The coupler 206 will yield when a force exerted thereon exceeds a threshold value. Upon removal of the coupler 206, the applicator 204 be coupled to a new clip assembly 202 in the same manner, to clip a second target portion of tissue. This process may be repeated as many times as needed, using the same applicator 204.

Figure 4:
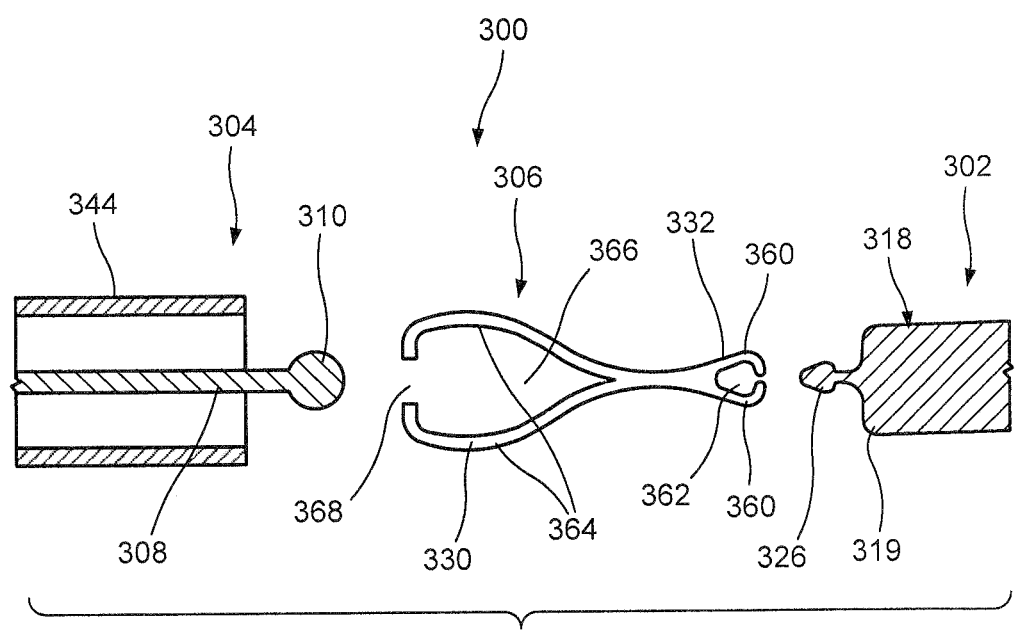
FIG. 4 shows a longitudinal cross-sectional view of a system according to a third exemplary embodiment of the present disclosure.

As shown in FIG. 4, a system 300 according to another exemplary embodiment substantially similar to the systems 100, 200 described above, comprises a clip assembly 302 to be loaded onto an applicator 304. In particular, a connector 318, which connects proximal ends of clip arms, is releasably coupled to a distal end 310 of a control member 308 of the applicator 304 via a coupler 306. It is noted that although a capsule and the clip arms of the clip assembly 302 are not shown, the clip assembly 302 may be substantially similar to the clip assembly 102 described above, the clip assembly 302 including clip arms connected to one another at proximal ends via the connector 318, which is slidably received within the capsule to move the clip arms between a tissue receiving configuration and a tissue gripping configuration. The connector 318, however, includes a protrusion 326 at a proximal end 319 thereof for connection to the coupler 306. The applicator 304 is substantially similar to the applicator 104 described above, including a catheter 344 and a control member 308 extending therethrough.

The coupler 306 includes a distal portion 332 sized and shaped to receive the protrusion 326 of the connector 318 and a proximal portion 330 sized and shaped to receive an enlarged distal end 310 of the control member 308. As described above with respect to systems 100, 200, the coupler 306 may be pre-assembled onto the connector 318 of the clip arms 312. The distal portion 332 may, for example, include a pair of opposed arms 360 defining a space 362 therebetween, the space 362 sized and shaped to receive the protrusion 326 therein. The pair of opposed arms 360 may be snapped over the protrusion 326 so that the protrusion 326 is held within the space 362.

Similarly, the proximal portion 330 may include a pair of opposed arms 364 defining a space 366 therebetween, the space 366 sized and shaped to receive the enlarged distal end 310 of the control member 308. The opposed arms 364 are designed to spread apart when the enlarged distal end 310 is pressed distally thereagainst so that the enlarged distal end may be moved distally past a proximal opening 368 of the space 366 and into the space 366. Once the enlarged distal end 310 is received within the space 366, the opposed arms 366 revert back to their original shape, holding the enlarged distal end in the space 366 between the opposed arms 364. Thus, the control member 308 is substantially fixed relative to the coupler 306, and the clip arms 312 to which the coupler 306 is connected, so that a longitudinal movement of the control member 308 relative the capsule and/or the catheter 344 moves the clip assembly 302 between the tissue receiving configuration and the tissue gripping configuration.

A force required to disengage the coupler 306 from the connector 318 is smaller than a force required to disengage the coupler 306 from the enlarged distal end 310 of the connector 318. Thus, once target tissue has been gripped by the clip assembly 302 as desired, the control member 308 may be drawn proximally relative to the capsule until a force exerted on the distal portion 332 exceeds a predetermined threshold value, causing the opposed arms 360 thereof to yield, releasing the protrusion 326 of the connector 318 therefrom. The control member 308 is then disengaged from the clip arms so that the applicator 304 may be withdrawn from the body leaving the clip assembly 302 clipped over the target tissue. The coupler 306 remains attached to the control member 308 as the applicator 304 is withdrawn from the body. Once the applicator 304 is withdrawn from the body, the coupler 306 may be removed therefrom by pulling the coupler 306 from the enlarged distal end 310 with enough force to cause the opposed arms 364 of the proximal portion 330 of the coupler 306 to yield, releasing the enlarged distal end 310 therefrom. Upon removal of the coupler 306, the applicator 304 may be coupled to a new clip assembly 302 in the same manner, to clip a second target portion of tissue. This process may be repeated as many times as needed, using the same applicator 304.

Although the exemplary embodiments show and describe specific systems 100-300 configured for loading clip assemblies onto an applicator via a coupler, it will be understood by those of skill in the art that the present disclosure includes any of a variety of couplers for coupling a connector of a clip assembly to a control member of an applicator, so long as the coupler may be pre-assembled with the connector and yields, fractures and/or is otherwise separable from the connector during deployment of the clip assembly. Once the clip assembly has been deployed, the coupler (or a remaining portion thereof) may be removed from the control member of the applicator so that the applicator may be loaded with a new clip assembly.

It will be apparent to those skilled in the art that various modifications may be made in the present disclosure, without departing from the scope of the disclosure.

What is claimed is:

1. A system for treating tissue, comprising:
a first clip assembly including a pair of clip arms, each of the clip arms of the first clip assembly extending from a proximal end to a distal end, the proximal end of each of the clip arms of the first clip assembly being slidably received within a channel of a first capsule to be moved between a tissue receiving configuration, in which distal ends of the clip arms of the first clip assembly are separated from one another, and a tissue clipping configuration, in which distal ends of the clip arms of the first clip assembly are moved toward one another, wherein the clip arms of the first clip assembly are biased toward the tissue receiving configuration and the clip arms of the first clip assembly are closed when received within the channel of the first capsule;
a connector connecting proximal ends of the clip arms of the first clip assembly to one another;
an applicator including a catheter and a control member extending therethrough, the control member configured to move the clip assembly between the tissue receiving configuration and the tissue clipping configuration;
a coupler releasably coupled to the connector and configured to be coupled to the distal end of the control member, the coupler configured to yield when a proximal force exerted on the coupler via the control member exceeds a first predetermined threshold value to disengage the clip arms and deploy the first clip assembly, wherein a distal portion of the coupler includes a plurality of fingers movable between a biased engaging configuration, in which a tab of each of the fingers engages the proximal end of a corresponding one of the clip arms, and a non-engaging configuration in which the tabs are moved out of engagement with the clip arms; and
a second clip assembly releasably coupleable to the coupler, the second clip assembly including a pair of clip arms, each of the clip arms of the second clip assembly extending from a proximal end to a distal end, the proximal end of each of the clip arms of the second clip assembly being slidably received within a channel of a second capsule and configured to be releasably coupled to the coupler after the first clip assembly has been deployed therefrom so that the clip arms of the second clip assembly are movable relative to the second capsule between a tissue receiving configuration, in which distal ends of the clip arms of the second clip assembly are separated from one another, and a tissue clipping configuration, in which distal ends of the clip arms of the second clip assembly are moved toward one another.

2. The system of claim 1, wherein the coupler includes a lumen extending therethrough, the lumen including a first tapered portion tapering from a proximal end toward a narrow opening that deforms when a distal force exerted thereon by an enlarged distal end of the control member exceeds a second predetermined threshold value so that the enlarged distal end may be moved distally therepast to couple the control member to the coupler.

3. The system of claim 2, wherein the lumen of the coupler includes a second tapered portion flaring outward from the narrow opening to a distal end so that when the enlarged distal end of the control member is moved proximally against the second tapered portion, the plurality of fingers is moved from the engaging configuration to the non-engaging configuration.

4. The system of claim 1, wherein the distal end of a first one of the clip arms includes a tip extending radially inward toward a radially inwardly extending tip of the other clip arm.

5. The system of claim 1, further comprising a locking feature configured to lock the clip arms in the tissue gripping configuration.

* * * * *